United States Patent
Makino

(10) Patent No.: US 12,029,385 B2
(45) Date of Patent: Jul. 9, 2024

(54) ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 784 days.

(21) Appl. No.: 17/251,937

(22) PCT Filed: Sep. 18, 2019

(86) PCT No.: PCT/JP2019/036646
§ 371 (c)(1),
(2) Date: Dec. 14, 2020

(87) PCT Pub. No.: WO2020/066807
PCT Pub. Date: Apr. 2, 2020

(65) Prior Publication Data
US 2021/0259515 A1   Aug. 26, 2021

(30) Foreign Application Priority Data
Sep. 27, 2018   (JP) .................................. 2018-182066

(51) Int. Cl.
*A61B 1/00*   (2006.01)
*G06T 7/00*   (2017.01)

(52) U.S. Cl.
CPC ...... *A61B 1/00006* (2013.01); *A61B 1/00004* (2013.01); *A61B 1/000094* (2022.02);
(Continued)

(58) Field of Classification Search
CPC ............ A61B 1/00004; A61B 1/00006; A61B 1/000094; A61B 1/0005
See application file for complete search history.

(56) References Cited

U.S. PATENT DOCUMENTS

| | | | |
|---|---|---|---|
| 8,538,113 B2 * | 9/2013 | Tanaka | A61B 5/1075 382/131 |
| 2006/0280347 A1 * | 12/2006 | Shirahata | A61B 6/463 382/128 |

(Continued)

FOREIGN PATENT DOCUMENTS

| | | |
|---|---|---|
| JP | 2016-039874 | 3/2016 |
| JP | 2018-515197 | 6/2018 |

(Continued)

OTHER PUBLICATIONS

May 22, 2023 Chinese Office Action in corresponding Chinese Application No. 201980040779.0, and partial machine English translation thereof.

(Continued)

*Primary Examiner* — Aaron B Fairchild
(74) *Attorney, Agent, or Firm* — Greenblum & Bernstein, P.L.C.

(57) ABSTRACT

An electronic endoscope system includes an electronic endoscope, a processor that includes an evaluation unit, and a monitor. The evaluation unit includes an evaluation value calculation unit that calculates a lesion evaluation value indicating the intensity of lesion in the living tissue in each of the images, an imaging position information acquisition unit that acquires information on the imaging position of each image, a lesion position calculation unit that determines the presence or absence of the lesion based on whether the lesion evaluation value exceeds a predetermined threshold and obtains a start position and an end position of a region of a lesion portion, and an organ lesion evaluation unit that evaluates a degree of lesion in the organ using a length of the lesion portion calculated from the start position and the end position and a representative value of the lesion evaluation value.

9 Claims, 7 Drawing Sheets

(52) U.S. Cl.
CPC .......... *A61B 1/0005* (2013.01); *G06T 7/0012* (2013.01); *G06T 2207/10068* (2013.01); *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 2010/0092055 A1* | 4/2010 | Matsuda | G06T 7/187 |
| | | | 382/128 |
| 2012/0197134 A1* | 8/2012 | Okawa | A61B 1/00096 |
| | | | 600/476 |
| 2017/0150904 A1* | 6/2017 | Park | A61B 1/00009 |
| 2018/0108138 A1 | 4/2018 | Kluckner et al. | |
| 2018/0279866 A1 | 10/2018 | Makino | |
| 2019/0192048 A1 | 6/2019 | Makino et al. | |

FOREIGN PATENT DOCUMENTS

| | | |
|---|---|---|
| WO | 2017/057680 | 4/2017 |
| WO | 2018/043550 | 3/2018 |

OTHER PUBLICATIONS

Triana Lobaton et al., "The Modified Mayo Endoscopic Score (MMES): A New Index for the Assessment of Extension and Severity of Endoscopic Activity in Ulcerative Colitis Patients", Journal of Crohn's and Colitis, 2015, pp. 846-852.

"To everyone of ulcerative colitis, Basic knowledge necessary for treatment you want to know, FY 2017 results of research conducted with the assistance of the Health and Labor Sciences Research Grant (Policy research business for intractable diseases or the like (Policy research business for intractable diseases)", The research team on intractable inflammatory bowel disease (Suzuki Group), Third Edition, non-official translation, Apr. 2018, pp. 1-17.

Official Communication issued in International Bureau of WIPO Patent Application No. PCT/JP2019/036646, dated Dec. 3, 2019.

* cited by examiner

ELECTRONIC ENDOSCOPE SYSTEM

TECHNICAL FIELD

The present invention relates to an electronic endoscope system that evaluates the degree of lesion in an organ by imaging a living tissue in the organ.

BACKGROUND ART

Lesion portions in a living tissue have varying levels of severity, from inflammation in which a mucosal layer of the living tissue becomes thin and rough and red, to ulcers that are partially missing from the mucosal layer and its lower layers. For example, the ulcerative part of an ulcerative colitis (UC) lesion includes white moss and purulent mucus to be white, and the inflamed portion shows red with edema and easy bleeding. Such lesion portions can be imaged and observed with an endoscope system.

However, it is necessary to undergo long-term training under the guidance of a skilled person in order for an operator to be able to distinguish between a normal portion (also referred to as a healthy portion) and a lesion portion by the difference in color contained in an image of the endoscope. In addition, it is not easy for even a skilled operator to identify a lesion portion from a slight color difference, and careful work is required. Therefore, it is preferable that the endoscope system provides an evaluation result in which the degree of lesion in the lesion portion in the organ is objectively quantified.

On the other hand, there is known an endoscope system that can suppress fluctuations in the evaluation value of the inflamed portion due to the brightness of the image to stably calculate the evaluation value, and suppress the processing load of the calculation of the evaluation value (Patent Literature 1).

CITATION LIST

Patent Literature

Patent Literature 1: WO 2017/057680 A

SUMMARY OF INVENTION

Technical Problem

The above-mentioned endoscope system includes a light source device that irradiates an object with illumination light, an image acquisition unit that captures the reflected light from the object with an image sensor and acquires a color image containing at least three or more color components, and an evaluation unit obtains an evaluation result regarding a target disease of each pixel based on an angle formed by a line segment connecting a predetermined reference point set in a color plane and a pixel correspondence point in a color plane of each pixel of the color image acquired by the image acquisition unit and a reference axis having a correlation with the target disease in the color plane defined by at least two or more color components among at least three or more color components. The reference axis is set so as to pass through the predetermined reference point. The reference axis is at least one of an axis having a correlation with a target disease showing an inflammation degree of a predetermined value or less and an axis having a correlation with a target disease showing an inflammation degree of a predetermined value or more in the color plane.

According to such a configuration, it is possible to suppress the fluctuation of the inflammation evaluation value due to the brightness of the image, perform stable calculation of the inflammation evaluation value, and suppress the processing load of the calculation of the inflammation evaluation value.

However, when the endoscope system evaluates a lesion of a living tissue in the organ, the evaluation is limited to the part of the living tissue from which the image has been taken. It is not possible to properly evaluate how much the intensity of the lesion portion has spread in the depth direction inside the organ and how wide the lesion portion is.

The degree of lesion (severity of lesion) in an organ is preferably evaluated by the intensity of lesion in the lesion portion and the extent of the lesion portion, but the conventional endoscope system is not possible to comprehensively evaluate the degree of lesion in the organ including the extent of the lesion portion.

Therefore, an object of the invention is to provide an electronic endoscope system which is capable of comprehensively evaluating the degree of lesion in an organ based on the intensity of lesion in the lesion portion and the extent of the lesion portion when evaluating the degree of lesion in an organ (severity of lesion).

Solution to Problem

One aspect of the invention is an electronic endoscope system that evaluates a lesion of a living tissue inside an organ. The electronic endoscope system includes
  an electronic endoscope configured to image a living tissue in an organ,
  a processor that includes an evaluation unit configured to process a plurality of captured images of the living tissue to evaluate the degree of lesion in the organ, and
  a monitor configured to display an evaluation result of the lesion in a screen.
  The evaluation unit includes
  an image evaluation value calculation unit configured to calculate an image evaluation value indicating an intensity of lesion of the living tissue in each of the images from the pixel evaluation value for each of the plurality of images of the living tissue,
  an imaging position information acquisition unit configured to acquire information of an imaging position inside the organ in which each of the images is captured in association with each of the images,
  a lesion position calculation unit that determines presence or absence of the lesion in each of the images based on whether the image evaluation value exceeds a predetermined threshold so as to obtain a start position and an end position of a region of a lesion portion in which the lesion is continuously spreading in a depth direction inside the organ, and
  an organ lesion evaluation unit configured to set a length of the lesion portion to be evaluated from the start position and the end position as extent information of the lesion portion, and evaluate the degree of lesion in the organ using the extent information and a representative value of the image evaluation value of a captured lesion portion image obtained by imaging the lesion portion.

It is preferable that the lesion position calculation unit uses, when the lesions exist at a plurality of locations, one having a maximum length in the depth direction in which the lesion is continuously spread as the lesion portion to be evaluated.

Another aspect of the invention is an electronic endoscope system that evaluates a lesion of a living tissue inside an organ. The electronic endoscope system includes
an electronic endoscope configured to image a living tissue in an organ,
a processor that includes an evaluation unit configured to process a plurality of captured images of the living tissue to evaluate the degree of lesion in the organ, and
a monitor configured to display an evaluation result of the lesion in a screen.

The evaluation unit includes
an image evaluation value calculation unit configured to calculate a pixel evaluation value indicating an intensity of lesion of the living tissue in each of the plurality of images of the organ for each pixel of the plurality of images of the living tissue, and calculate an image evaluation value indicating an intensity of lesion of the living tissue in each of the images from the pixel evaluation value,
an imaging position information acquisition unit configured to acquire information of an imaging position inside the organ in which each of the images is captured in association with each of the images,
a lesion position calculation unit that determines presence or absence of the lesion in each of the images based on whether the image evaluation value exceeds a predetermined threshold, and obtains a start position and an end position of a lesion portion in which the lesion is continuously spreading in a depth direction inside the organ, and
an organ lesion evaluation unit configured to set area information of the lesion portion, which is set from a pixel having the pixel evaluation value equal to or more than a threshold for determining the lesion in the plurality of captured lesion portion images obtained by imaging the lesion portion between the start position and the end position, as extent information of the lesion portion, and evaluate the degree of lesion to be evaluated in the organ using the extent information and a representative value of the image evaluation value in the captured lesion portion image.

It is preferable that the organ lesion evaluation unit obtains the area information based on the number of pixels obtained by counting pixels of which the pixel evaluation value is equal to or greater than a threshold for determining the lesion in the captured lesion portion image.

It is preferable that the organ lesion evaluation unit obtains the area information based on a product of an average value in the captured lesion portion image of an occupancy ratio, in the captured lesion portion image, of pixels of which the pixel evaluation value is equal to or greater than the threshold for determining the lesion and a length of the lesion portion to be evaluated calculated from the start position and the end position.

It is preferable that the representative value is a maximum value among the image evaluation values of the captured lesion portion image.

It is preferable that the organ lesion evaluation unit has a lesion sample correspondence, for each of the lesion samples obtained using an image group including images of a plurality of lesion samples, which is obtained by capturing images of the inside of the organ, having a determined evaluation level of the degree of lesion, among a lesion sample representative value of the lesion sample corresponding to the representative value, lesion sample extent information of the lesion sample corresponding to the extent information of the lesion portion, and the evaluation level.

The organ lesion evaluation unit evaluates the degree of lesion to be evaluated at the level using the lesion sample correspondence from the extent information of the lesion portion to be evaluated obtained by imaging an inside of the organ and the representative value of the lesion portion to be evaluated.

Further, it is preferable that the organ lesion evaluation unit is a predictive model for predicting the evaluation level of the lesion portion to be evaluated, sets a lesion sample representative value of a lesion sample corresponding to the representative value, lesion sample extent information of the lesion sample corresponding to the extent information of the lesion portion, and the evaluation level as learning data for each of the lesion samples obtained using an image group including images of a plurality of lesion samples having a determined evaluation level of the degree of lesion, and includes a predictive model obtained by machine-learning a correspondence between the lesion sample representative value, the lesion sample extent information, and the evaluation level.

The organ lesion evaluation unit causes the predictive model to predict an evaluation level of the lesion portion to be evaluated from the representative value of the lesion portion to be evaluated and the extent information of the lesion portion.

It is preferable that the monitor displays a two-dimensional scatter diagram in a screen, in which the representative value of the lesion portion to be evaluated and the extent information of the lesion portion to be evaluated are plotted together with the lesion sample representative value and the lesion sample extent information.

Advantageous Effects of Invention

According to the above-mentioned electronic endoscope system, when evaluating the degree of lesion in an organ (severity of lesion), the degree of lesion in the organ can be comprehensively determined by the intensity of lesion in the lesion portion and the extent of lesion portion.

DESCRIPTION OF EMBODIMENTS

Figure 1:
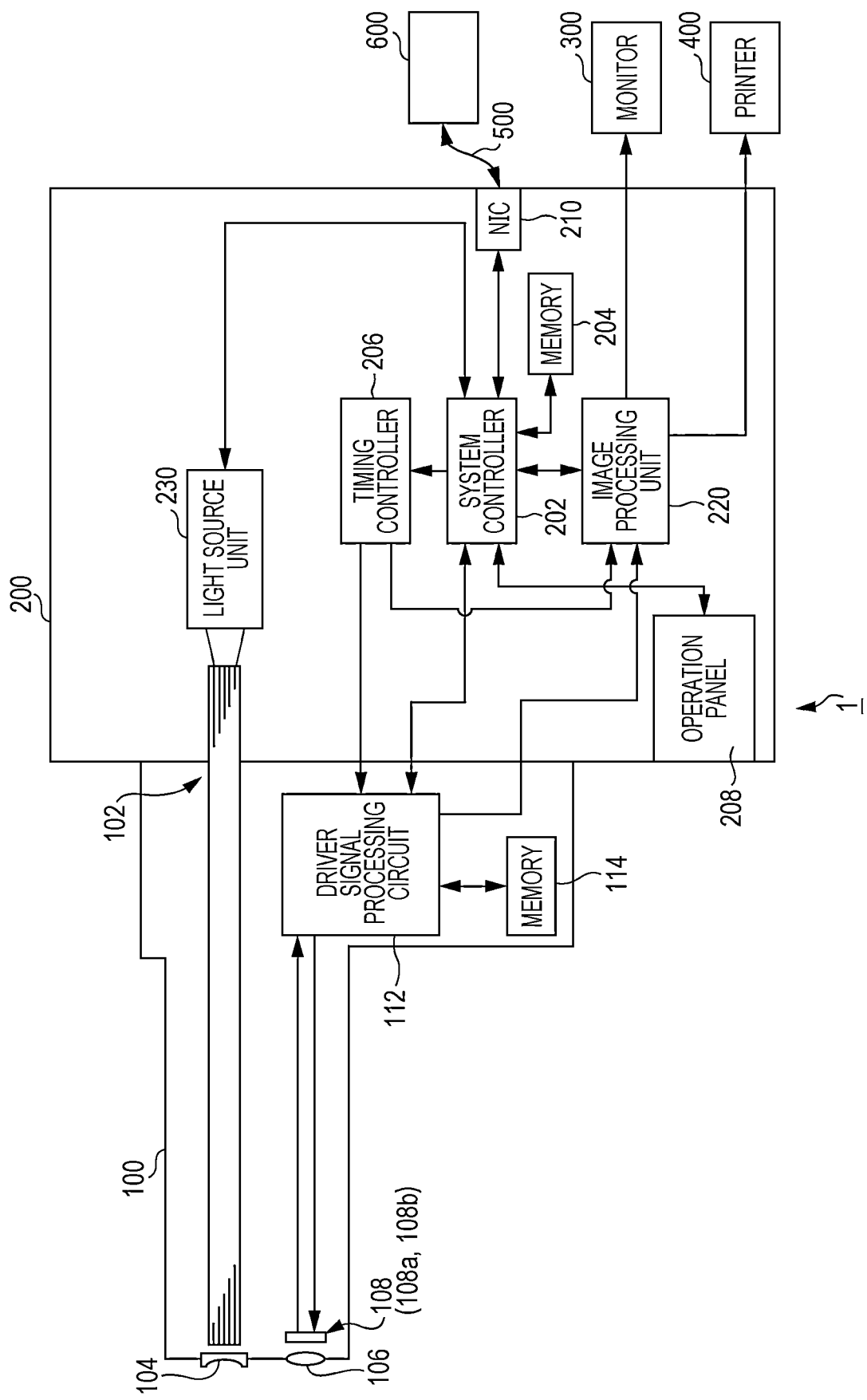
FIG. 1 is a block diagram illustrating a configuration of an endoscope system according to an embodiment.

Hereinafter, before explaining an electronic endoscope system of an embodiment of the invention with reference to the drawings, first, the evaluation of the degree of lesion in the organ will be conceptually described.
(Outline Explanation of Evaluation of Degree of Lesion)

In the embodiments described below, the degree of lesion is evaluated by processing an image of a living tissue in an organ imaged by an electronic endoscope. The degree of lesion in an organ is comprehensively evaluated using the extent of lesion and the intensity of lesion, which represents the degree of progression of the lesion at each location. When imaging a living tissue in an organ, for example, an electronic scope is inserted from the open end of a tubular organ to the deepest position inside the organ to be imaged in the depth direction (including a direction toward the back side and a direction toward the opening side opposite to the back side), and captures the images of the living tissue inside the organ while moving substantially toward the open end of the organ from there.

The captured images of the living tissue may be moving images continuously captured at certain time intervals, or may be still images captured intermittently while moving the electronic endoscope in the organ. In the case of moving images, it is preferable to take an image while moving the electronic endoscope in the same direction at substantially the same moving speed.

In the evaluation of the degree of lesion within an organ, for example, an image evaluation value indicating the intensity of lesion in the living tissue in each image is calculated for each of a plurality of images of the living tissue illuminated by a white light. This image evaluation value is not particularly limited, but may be an inflammation evaluation value for evaluating the intensity of inflammation of the lesion portion (inflamed portion) based on the information (for example, redness) of the color component of a lesion portion, for example, when the lesion is inflammation.

The organ to be evaluated is not particularly limited, and examples thereof may include a digestive tract such as pharynx to esophagus, stomach, small intestine, and large intestine.

Further, for example, a living tissue is illuminated and imaged using special light including a laser beam having a wavelength of 405 nm, a laser beam having a wavelength of 445 nm, and fluorescence of 445 to 700 nm obtained by emitting a fluorescent body with a laser beam having a wavelength of 445 nm. Then, the ratio of two image signals is created from the three RGB image signals obtained by imaging, and the evaluation value for each image created by using the processing result of a predetermined highlight processing on these two image signals, for example, an evaluation value for evaluating mucosa or the like in atrophic gastric inflammation, can be used as the image evaluation value.

Further, for example, a living tissue is illuminated with the light having a wavelength of 600 nm, the light having a wavelength of 630 nm, and the light having a wavelength of 540 nm as illumination light and image, and a processing result obtained by performing a predetermined highlight processing on the image obtained by illumination to create an evaluation value for each image, for example, an evaluation value for evaluating the state of blood vessels of the deep mucosa can be used as the image evaluation value.

In addition, the cells of the mucosa of the digestive tract, which are illuminated with light and have been pretreated by staining or the like, are magnified and imaged, and an average value of the feature quantities (shape information of length, diameter, circumference, roundness, etc.) of the cell nuclei can be used the evaluation value for evaluating the intensity of lesion such as non-tumor, adenoma, cancer, and the like as the image evaluation value.

Further, the image evaluation value may be an evaluation level such as a Mayo score obtained for each image. In this case, a representative value of the image evaluation value of the lesion portion, which is obtained from the image of the lesion sample of the lesion portion imaged in advance, the extent information (described later) of the lesion portion, and the evaluation level such as the Mayo score are used as learning data so as to make a predictive model machine-learn the correspondence among the representative value, the extent information of the lesion portion, and the evaluation level. Using the machine-learned predictive model, the evaluation level is predicted from the representative value of the image evaluation value of the lesion portion obtained from the newly captured image of the living tissue in the organ and the extent information (described later) of the lesion portion. Further, the image evaluation value may be a numerical value of the histopathological evaluation for each image.

Further, when each image is captured, the information of the imaging position in the organ whose image is captured is associated with each image and the image is acquired. The information on the imaging position can be obtained, for example, by providing a sensor capable of detecting the position information in the vicinity of the image sensor at the tip end portion of the electronic scope inserted into the organ. In addition, the organ can be divided into a plurality of segments having identifiable features, and the segment in which the tip end portion of the electronic scope is located can be used as position information. In this case, the characteristics of the segments in the captured image is extracted by image processing to specify the segment of the imaging position, and the position information regarding which segment the tip end portion of the electronic scope is located can be obtained. In addition, the operator presses a preset button while viewing the image displayed on the monitor, and inputs a signal indicating that the tip end portion of the electronic scope has started passing through a predetermined segment. Thus, it is also possible to obtain position information regarding which segment the tip end portion of the electronic scope is located.

Further, in the embodiment described below, the presence or absence of a lesion in each image is determined based on whether the calculated image evaluation value exceeds a predetermined threshold, and a start position and an end position of the region of the lesion portion where the lesion is continuously spreading in the depth direction in the organ.

The length of the lesion portion to be evaluated calculated from the obtained start position and end position is used as the extent information, and the degree of lesion in the organ is evaluated using the extent information and the representative value of the image evaluation value of the captured lesion portion image of the lesion portion obtained by imaging the lesion portion to be evaluated.

Here, the representative value may be, for example, a maximum value, a median value, or an average value, but is preferably the maximum value in that the intensity of lesion can be accurately evaluated.

In the evaluation of the degree of lesion in the organ, for example, the degree of lesion is preset to be divided into a plurality of levels, and the degree of lesion in the organ is evaluated by the level according to this setting. Further, the extent information and the information of the representative value of the image evaluation value may be displayed on the monitor, or the two-dimensional scatter diagram obtained by plotting these information on a plane may be displayed on the monitor together with the above level.

In this way, the length of the lesion portion to be evaluated calculated from the start position and the end position of the lesion portion to be evaluated is used as the extent information, and the degree of lesion in the organ is evaluated using the extent information and the representative value of the image evaluation value of the captured lesion portion image of the lesion portion obtained by imaging the lesion portion to be evaluated, so that the degree of lesion in the organ can be comprehensively evaluated.

For example, it is possible to distinguish between the morphology of a lesion having a low representative value of the image evaluation value and a large extent of the lesion portion and the morphology of a lesion having a large representative value of the image evaluation value and a small extent of the lesion portion.

In addition, regarding the information on the extent of lesion, in each of the captured lesion portion images obtained by imaging the lesion portion between the start position and the end position, the area information of the lesion portion determined from the pixels determined as the part of the lesion in the captured lesion portion image can also be used instead of the length of the lesion portion calculated from the start position and the end position of the lesion portion. As will be described later, it is possible to determine whether the pixel determined as the lesion portion in the captured lesion portion image is a lesion portion by using the pixel evaluation value for each pixel used when calculating the image evaluation value. For example, when the lesion described later is inflammation, the living tissue redness (pixel evaluation value) is calculated for each pixel in order to calculate the inflammation evaluation value as an image evaluation value. In this case, it can be determined whether it is a lesion portion depending on whether the living tissue redness has a value equal to or greater than a threshold for determining the lesion defined in advance. Therefore, the area information of the lesion portion can be determined from the pixels determined to be the lesion in the captured lesion portion image. In this case, it is preferable to adjust the frame rate of imaging or the moving speed of the electronic scope so that the same lesion portion is not duplicated in the different captured lesion portion image.

(Electronic Endoscope System)

FIG. 1 is a block diagram illustrating an example of a configuration of an electronic endoscope system 1 of this embodiment of the invention. As illustrated in FIG. 1, the electronic endoscope system 1 includes an electronic scope 100, an electronic endoscopy processor 200, a monitor 300, and a printer 400.

The electronic endoscopy processor 200 includes a system controller 202 and a timing controller 206. The system controller 202 executes various programs stored in a memory 204 and integrally controls the entire electronic endoscope system 1. Further, the system controller 202 changes various settings of the electronic endoscope system 1 according to an instruction by the user (operator or assistant) input to an operation panel 208. The timing controller 206 outputs a clock pulse for adjusting the operation timing of individual units to individual circuits in the electronic endoscope system 1.

The electronic endoscopy processor 200 includes a light source unit 230 that supplies illumination light to the electronic scope 100. Although not illustrated, the light source unit 230 includes, for example, a high-brightness lamp that emits white illumination light by receiving drive power from a lamp power source, for example, a xenon lamp, a metal halide lamp, a mercury lamp, or a halogen lamp. The light source unit 230 is configured such that the illumination light emitted from the high-brightness lamp is focused by a condensing lens (not illustrated) and then incident on the incident end of an LCB (Light Carrying Bundle) 102 of the electronic scope 100 via a dimmer (not illustrated).

Alternatively, the light source unit 230 includes a plurality of light emitting diodes that emit light in a wavelength band of a predetermined color. The light source unit 230 is configured such that the light emitted from the light emitting diode is synthesized using an optical element such as a dichroic mirror, and the combined light is collected as illumination light by a condensing lens (not illustrated), and then incident on the incident end of the LCB (Light Carrying Bundle) 102 of the electronic scope 100. A laser diode may be used instead of the light emitting diode. The light emitting diode and the laser diode have features such as low power consumption and low heat generation amount as compared with other light sources, and therefore have an advantage that bright images can be acquired while suppressing power consumption and heat generation amount. By acquiring a bright image, it is possible to improve the accuracy of the evaluation value regarding inflammation described later.

In the example illustrated in FIG. 1, the light source unit 230 is built in the electronic endoscopy processor 200, but may be provided in the electronic endoscope system 1 as a device separate from the electronic endoscopy processor 200. Further, the light source unit 230 may be provided at the tip end portion of the electronic scope 100 described later. In this case, the LCB 102 that guides the illumination light is unnecessary.

The illumination light incident on the LCB 102 from the incident end propagates in the LCB 102 and is emitted from the end of the LCB 102 arranged in the tip end portion of the electronic scope 100, and is emitted to the living tissue inside the organ, which is the object, through a light distribution lens 104. The reflected light from the living tissue forms an optical image on the light receiving surface of a solid-state image sensor 108 via an objective lens 106.

The solid-state image sensor 108 is, for example, a single-plate color CCD (Charge-Coupled Device) image sensor in which various filters such as an IR (Infrared) cut filter 108a and a Bayer-arranged color filter 108b are arranged on the light receiving surface, and generates primary color signals of R (Red), G (Green), and B (Blue) according to the optical image formed on the light receiving surface. Instead of the single-plate color CCD image sensor, a single-plate color CMOS (Complementary Metal Oxide Semiconductor) image sensor can also be used. CMOS image sensors generally tend to have an overall darker image than CCD image sensors. Therefore, the advantageous effect of suppressing the fluctuation of the severity of the lesion in the lesion portion due to the brightness of the image is more remarkable than when using the CMOS image sensor in the numerical processing for evaluating the degree of lesion described below. In this way, the electronic scope 100 uses the solid-state image sensor 108 to image the living tissue inside the organ and generate a moving image.

A driver signal processing circuit 112 is provided in a connection portion where the electronic scope 100 is connected to the processor 200. The driver signal processing circuit 112 generates an image signal (brightness signal Y, color difference signals Cb and Cr) by performing predetermined signal processing such as color interpolation and matrix calculation on the primary color signal input from the solid-state image sensor 108, and outputs the generated image signal to an image processing unit 220 of the electronic endoscopy processor 200. The driver signal processing circuit 112 also accesses a memory 114 and reads out device-specific information of the electronic scope 100. The device-specific information of the electronic scope 100 recorded in the memory 114 includes, for example, the number of pixels and sensitivity of the solid-state image sensor 108, an operable frame rate, a model number, or the like. The driver signal processing circuit 112 outputs the device-specific information read from the memory 114 to the system controller 202.

The system controller 202 performs various calculations based on the information stored in the memory 204 and the device-specific information of the electronic scope 100, and generates a control signal. The system controller 202 controls the operation and timing of various circuits in the electronic endoscopy processor 200 using the generated control signal so as to perform processing suitable for the electronic scope 100 connected to the electronic endoscopy processor 200.

The timing controller 206 supplies clock pulses to the driver signal processing circuit 112, the image processing unit 220, and the light source unit 230 in accordance with timing control by the system controller 202. The driver signal processing circuit 112 performs driving control of the solid-state image sensor 108 at a timing synchronized with the frame rate of the video image processed on the electronic endoscopy processor 200 side in accordance with the clock pulses supplied from the timing controller 206.

The image processing unit 220 is a portion capable of performing image processing according to an operator's instruction or according to preset processing contents. Under the control of the system controller 202, the image processing unit 220 generates a video signal for displaying an endoscopic image or the like on a monitor based on the image signal of the captured image input from the driver signal processing circuit 112, and outputs the video signal to the monitor 300. Further, as a part of image processing, the image processing unit 220 processes a plurality of captured images of the living tissue to evaluate the degree of lesion in the organ, and generates a video signal for displaying the evaluation result on a monitor, and outputs the video signal to the monitor 300. Specifically, the image processing unit 220 calculates an image evaluation value described later, which indicates the intensity of lesion of the living tissue in each image, from the plurality of images of the living tissue obtained by the electronic scope 100. The electronic scope 100 images the living tissue inside the organ at a set frame rate while continuously moving along the depth direction of the organ (also including a case where the imaging position in the depth direction is locally displaced in the opposite direction). For this reason, the image processing unit 220 specifies the position of the lesion portion using the image evaluation value of the moving image captured substantially continuously along the substantially depth direction and the information of the imaging position inside the organ in which each of the plurality of images is imaged so as to calculate the extent information of the depth direction of the organ of the lesion portion. Further, the image processing unit 220 calculates the representative value of the image evaluation value from the image evaluation values of the plurality of images obtained by imaging the lesion portion, that is, the plurality of captured lesion portion images, and evaluates the degree of lesion in the organ using the representative value and the extent information.

Further, the image processing unit 220 generates a color map image in which each pixel in the image is given a color according to a pixel evaluation value described later. The image processing unit 220 generates a video signal for displaying the information on the evaluation result of the degree of lesion in the organ and the color map image on the monitor, and outputs the video signal to the monitor 300. This allows the operator to evaluate the degree of lesion spreading in the depth direction of the organ of interest through the image displayed on the display screen of the monitor 300. The image processing unit 220 outputs the color map image and the information on the evaluation result of the degree of lesion in the organ to the printer 400 as needed.

The electronic endoscopy processor 200 is connected to a server 600 via a NIC (Network Interface Card) 210 and a network 500. The electronic endoscopy processor 200 can download information about endoscopic examination (for example, electronic medical record information of a patient, information of an operator, evaluation result of the degree of lesion in the same organ in the past) from the server 600. The downloaded information is displayed, for example, on the display screen of the monitor 300 or the operation panel 208. In addition, the electronic endoscopy processor 200 uploads the endoscopic examination results (endoscopic image data, examination conditions, evaluation results of the degree of lesion of an organ, operator's view, etc.) to the server 600 so as to store the results in the server 600.

Figure 2:
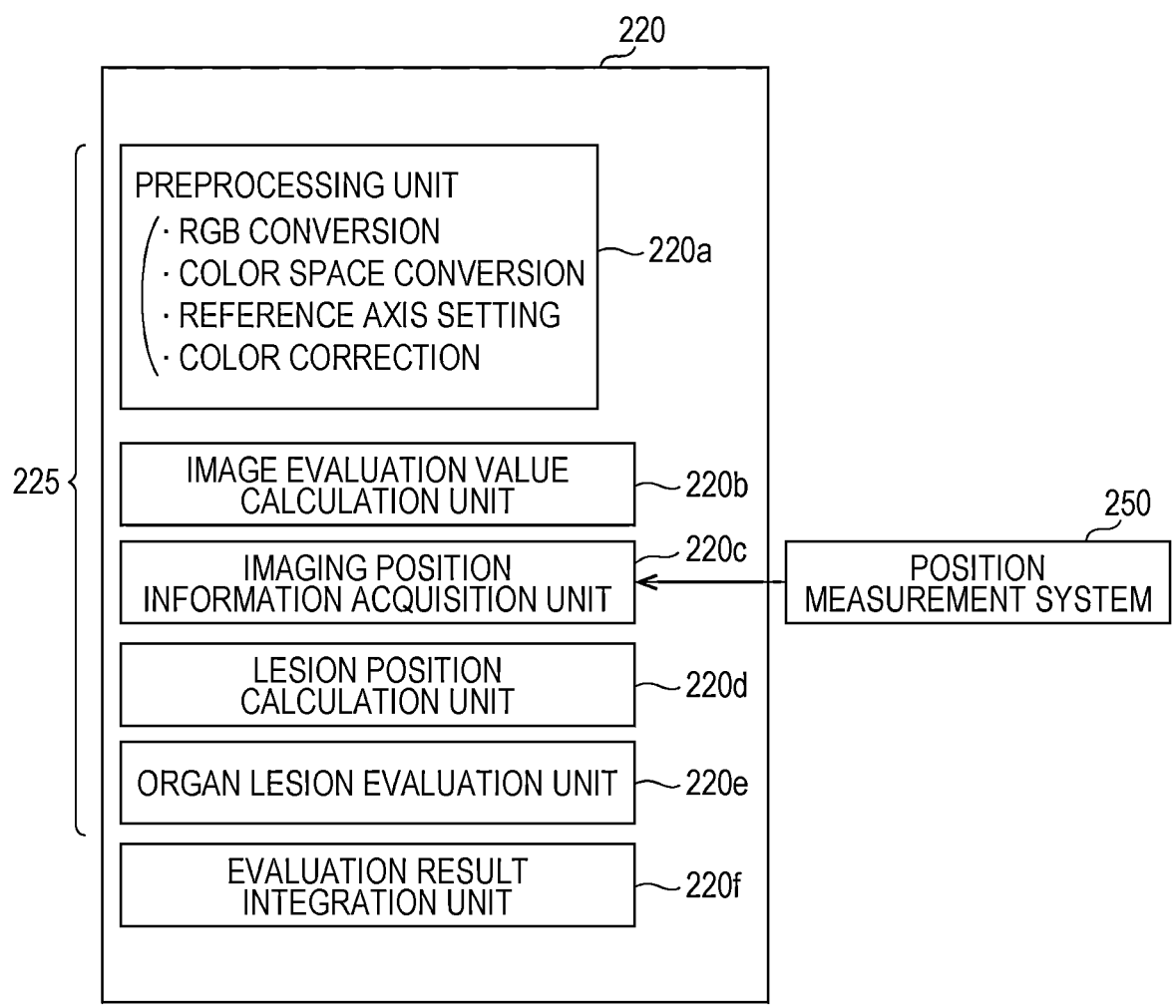
FIG. 2 is a diagram for explaining a configuration of a portion of the image processing unit illustrated in FIG. 1 for evaluating the extent of lesion in the depth direction of an organ.

FIG. 2 is a diagram for explaining the configuration of a part of the image processing unit 220 that evaluates the degree of lesion in an organ. The image processing unit 220 is a portion configured to process a plurality of images of a living tissue captured by the electronic scope 100 and evaluate the degree of lesion. The image processing unit 220 includes a preprocessing unit 220a, an image evaluation value calculation unit 220b, an imaging position information acquisition unit 220c, a lesion position calculation unit 220d, an organ lesion evaluation unit 220e, and an evaluation result integration unit 220f. The preprocessing unit 220a, the image evaluation value calculation unit 220b, the imaging position information acquisition unit 220c, the lesion position calculation unit 220d, and the organ lesion evaluation unit 220e forms an evaluation unit 225 which is configured to process a plurality of captured images of the living tissue so as to evaluate the degree of lesion in the organ.

The preprocessing unit 220a, the image evaluation value calculation unit 220b, the imaging position information acquisition unit 220c, the lesion position calculation unit 220d, the organ lesion evaluation unit 220e, and the evaluation result integration unit 220f may be a software module to be formed by activating a software program stored in the memory 204, or may be configured in hardware.

According to one embodiment, the image evaluation value calculation unit 220b evaluates the intensity of inflammation, which is an example of the intensity of lesion, for each image. Hereinafter, inflammation generated by ulcerative colitis or the like will be described as an example of a lesion.

The image evaluation value calculation unit 220b uses the living tissue redness, which is obtained by quantifying the degree of redness of the living tissue for each pixel, as the pixel evaluation value, and performs, for example, integration processing or averaging processing on the pixel evaluation values of the entire image to combine the values into one numerical value (inflammation evaluation value) so as to calculate an image evaluation value. That is, the degree of inflammation of the living tissue is evaluated by using the degree of redness of the living tissue. Hereinafter, a form for calculating the living tissue redness, which indicates the intensity of inflammation, will be described as an example.

The preprocessing unit 220a is a portion for preprocessing an image for evaluating the degree of redness exhibited by a living tissue. As illustrated as an example, the preprocessing unit 220a performs processing of RGB conversion, color space conversion, reference axis setting, and color correction.

The preprocessing unit 220a converts the image signal (brightness signal Y, color difference signals Cb and Cr) input from the driver signal processing circuit 112 into image color components (R, G, B) using predetermined matrix coefficients.

The preprocessing unit 220a further performs color conversion in which the image data converted into the image color component is normally projected onto the RG plane. Specifically, the image color component of each pixel in the RGB color space defined by three RGB primary colors is converted into the image color component of RG. Conceptually, the image color component of each pixel in the RGB color space is plotted in the RG plane according to the pixel values of the R and G components (for example, a section in the RG plane taking the pixel value of the R component=0 to 255 and the pixel value of the G component=0 to 255). Hereinafter, for convenience of explanation, the point of the image color component of each pixel in the RGB color space and the point of the image color component plotted in the RG color space are referred to as a "pixel correspondence point". The RGB image color components of the RGB color space are, for example, color components having wavelengths of 620 to 750 nm, wavelengths of 495 to 570 nm, and wavelengths of 450 to 495 nm, respectively. The color components constitute a color space (including a color plane). Hue and saturation are excluded from the "color components".

Further, the preprocessing unit 220a sets a reference axis in the RG plane necessary for evaluating the living tissue redness.

In the living tissue inside the organ of the patient to be an object, the R component among the image color components is dominant over the other components (G component and B component) due to the influence of the hemoglobin pigment and the like. When the degree of lesion in the lesion portion is low and the lesion portion is an inflamed portion, the stronger the inflammation, the stronger the red (R component) with respect to other colors (G component and B component). However, the color of the captured image in the organ changes depending on the imaging conditions that affect the brightness (for example, a condition under illumination light). Illustratively, a shaded area where the illumination light does not reach is black (achromatic color; for example, the values of the image color components of R, G, and B are zero or close to zero), and an area where the illumination light is strongly hit and reflected regularly is white (achromatic color; for example, when the values of the R, G, and B image color components are 8-bit shade, the values are 255 or close to 255). That is, even when the same inflamed portion where inflammation is occurring is imaged, the pixel value of the inflamed portion increases as the illumination light hits the image strongly. Therefore, depending on the condition under the illumination light, the value of the color component of the image may take a value that does not correlate with the intensity of inflammation.

In general, a healthy portion inside the organ having no inflammation is covered with sufficient mucosa. The mucosa is basically white, but the color is slightly yellowish, and the color (yellow) that appears on the image changes depending on the shading (thickness of the mucosa). Therefore, the shading of the mucosa is also considered to be one of the indexes for evaluating the intensity of inflammation. On the other hand, the inflamed portion inside the organ having inflammation is not sufficiently covered with mucosa. Specifically, as the blood vessels dilate, blood and body fluids leak from the blood vessels, so that the mucosa becomes relatively thin and the color of blood is easily visible. The mucosa is basically white, but the color is slightly yellowish, and the color (yellow) that appears on the image changes depending on the shading (thickness of the mucosa). Therefore, the shading of the mucosa is also considered to be one of the indexes for evaluating the degree of inflammation.

Figure 3:
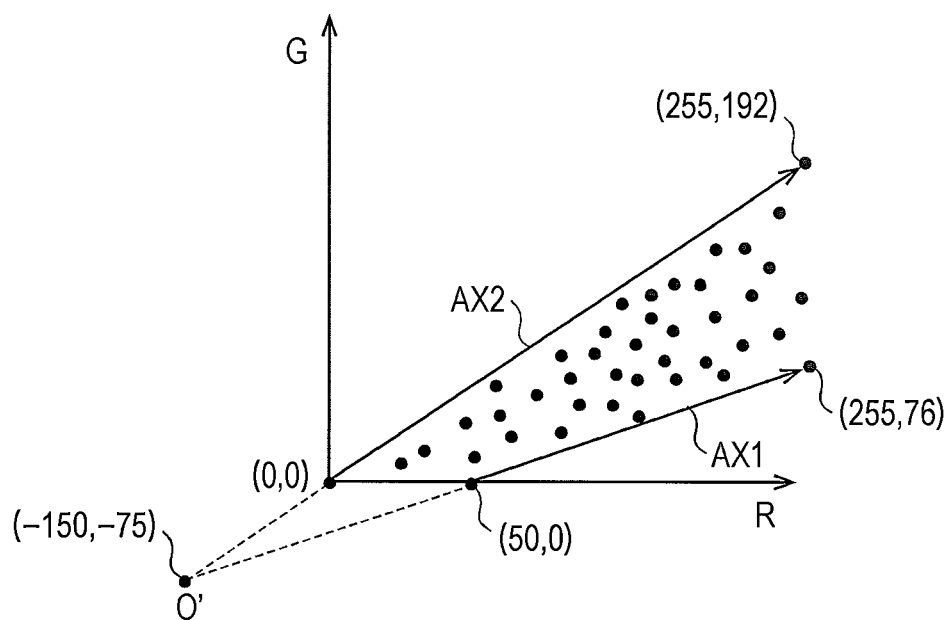
FIG. 3 is a diagram for explaining an example of a reference axis in a color space used in one embodiment.

Therefore, as illustrated in FIG. 3, the straight line passing through (50,0) and (255,76) is set as one of the reference axes in the RG color space, and the straight line passing through (0,0) and (255,192) is set as one of the reference axes. For convenience of explanation, the former reference axis is referred to as "hemoglobin change axis AX1", and the latter reference axis is referred to as "mucosal change axis AX2". FIG. 3 is a diagram for explaining an example of the reference axis in the color space used in one embodiment.

The plot illustrated in FIG. 3 is the result of analyzing a large number of reference images inside the organ. The reference images used for the analysis include the example of inflammatory image of each stage such as an example of an inflammatory image with the highest degree of inflammation (an example of an inflammatory image with the most severe level) and an example of an inflammatory image with the lowest degree of inflammation (an example of an image substantially considered to be a healthy portion). In the example illustrated in FIG. 3, only a part of the plot obtained as a result of the analysis is illustrated for the sake of clarifying the drawing. The actual number of plots obtained as a result of the analysis is much larger than the number of plots illustrated in FIG. 3.

As described above, the stronger the inflammation, the stronger the R component of the color components of the image is with respect to the other components (G component and B component). Therefore, the boundary line between the area where the plots are distributed and the area where the plots are not distributed, which is the axis on the boundary line closer to the R axis than the G axis, that is, the axis on the boundary line passing through (50,0) and (255,76) in the example illustrated in FIG. 3 is set as an axis having a high correlation with the portion having a highest degree of inflammation which is the portion having the highest degree of inflammation. This axis is the hemoglobin change axis AX1. On the hemoglobin change axis AX1, plots corresponding to the inflamed portion having the highest degree of inflammation imaged under various imaging conditions, for example, a condition under the illumination light, are superimposed. Therefore, the hemoglobin change axis AX1 is the axis on which the pixel correspondence points plotted are converged as the degree of inflammation of the living tissue increases.

On the other hand, the closer to the healthy portion, the stronger the G component (or B component) of the color components of the image is with respect to the R component. Therefore, the boundary line between the area where the plots are distributed and the area where the plots are not distributed, which is the axis on the boundary line closer to the G axis than the R axis, that is, the axis on the boundary line passing through (0,0) and (255,192) in the example illustrated in FIG. 3 is set as an axis having a high correlation with the portion having a lowest degree of inflammation which is a portion considered to be a substantially healthy portion. This axis is the mucosal change axis AX2. The mucosal change axis AX2 is superimposed with plots corresponding to various imaging conditions, for example, the portion having the lowest degree of inflammation imaged under illumination light, that is, what is considered to be a substantially normal portion. Therefore, the mucosal change axis AX2 is the axis on which the pixel correspondence points plotted converge as the degree of inflammation decreases (closer to the healthy portion).

In addition, the highest degree of lesion in the lesion portion is accompanied by bleeding. On the other hand, the portion having the lowest degree of lesion is a substantially normal healthy portion, and is therefore covered with sufficient mucosa. Therefore, the plot in the RG color space illustrated in FIG. 3 can be regarded as being distributed in the region sandwiched between the axis most correlated with blood (hemoglobin pigment) and the axis most correlated with the color of the mucosa. Therefore, of the boundary lines between the areas where the plots are distributed and the areas where the plots are not distributed, the boundary line closer to the R axis (strong R component) corresponds to the axis indicating the inflamed portion having the highest degree of inflammation (hemoglobin change axis AX1), and the boundary line closer to the G axis (strong G component) corresponds to the axis indicating the inflamed portion having the lowest degree of inflammation (mucosal change axis AX2).

After setting the reference axis in this way, a process of calculating the living tissue redness, which indicates the intensity of red, which will be described later, is performed on the color component of the normally projected image. Before the process of calculating the living tissue redness, color correction is performed on the normally projected pixel data.

The reference axis illustrated in FIG. 3 is an example, and the reference axis varies depending on the type of disease.

The preprocessing unit 220a performs color correction on the color components of the image represented in the RG color space before calculating the inflammation evaluation value. The correction matrix coefficient is stored in the memory 204. The preprocessing unit 220a corrects the pixel data (R, G), which is the pixel correspondence point in the RG color space of each pixel, as illustrated in the following equation using the correction matrix coefficient so that the inflammation evaluation values described later do not vary (in other words, to suppress inter-individual error of the electronic scope) when images are taken with different electronic endoscope systems despite the same inflamed portion.

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Corrected pixel data (R component)
$G_{new}$: Corrected pixel
Data (G component)
$M_{00}$ to $M_{11}$: Correction matrix coefficient
R: Pixel data before correction (R component)
G: Pixel data before correction (G component)

Figure 4:
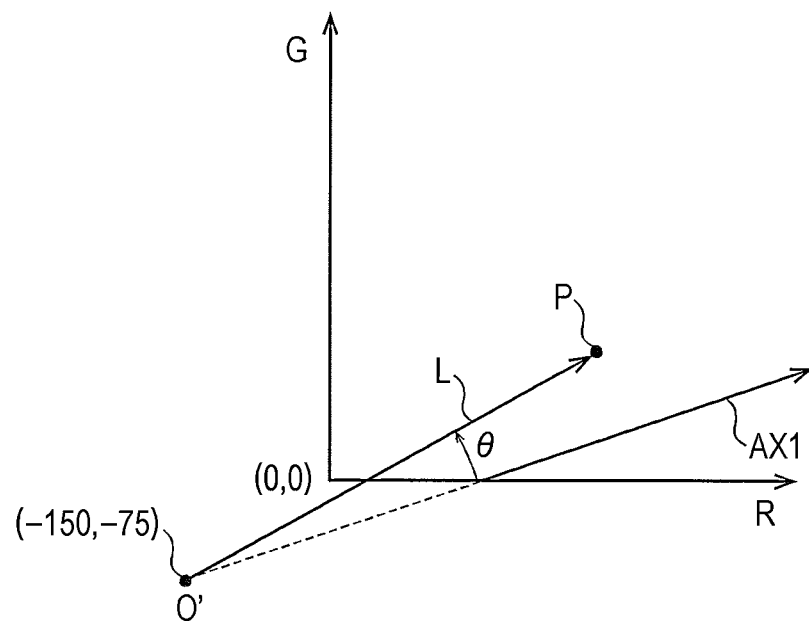
FIG. 4 is a diagram for explaining a method of calculating a deviation angle for calculating a living tissue redness used in one embodiment.

The image evaluation value calculation unit 220b selects one pixel of interest from the pixels, and calculates the deviation angle for calculating the degree of inflammation of the selected pixel of interest based on the information of the color component of the pixel of interest. That is, a quantification process is performed to quantify the degree of redness of the living tissue based on the information of the color component of the pixel. FIG. 4 is a diagram for explaining a method of calculating a deviation angle for calculating the living tissue redness used in one embodiment. Specifically, as illustrated in FIG. 4, the image evaluation value calculation unit 220b sets the intersection of the hemoglobin change axis AX1 and the mucosal change axis AX2 as a reference point O', and calculates the deviation angle θ at which the direction of the line segment L connecting the reference point O' and the pixel correspondence point P of the pixel of interest with respect to the hemoglobin change axis AX1. The reference point O' is located at the coordinates (−150, −75). The example in which the reference point O' is set to the coordinates (−150, −75) is given, but the invention is not limited to this. The reference point O' can be changed as appropriate, and may be, for example, the intersection of the R axis and the G axis in the RG color space.

A suitable coordinate position as the reference point O' is, for example, a position where an error in the evaluation result due to fluctuations in brightness can be reduced. Specifically, the reference point O' is preferably set by obtaining a point in advance where an error between the evaluation result in the dark portion (brightness is less than a predetermined value) and the evaluation result in the non-dark portion (brightness is more than a predetermined value) is minimized.

In addition, for example, if the reference point O' is set between the coordinates (−10, −10) and (10, 10), the coordinates (−150, −75) and the like are compared with the case where the reference point O' is set. Therefore, the amount of change in the angle θ when the pixel correspondence point changes becomes large, so that the resolution is improved. As a result, a highly accurate evaluation result can be obtained. On the other hand, by setting the reference point O' between the coordinates (−50, −50) and (−200, −200), the evaluation result indicating the intensity of inflammation is not easily affected by noises.

When the brightness of an image of a living tissue inside an organ changes depending on the condition under the white light, the color of the image is generally affected by individual differences, the location of the image, the state of inflammation, etc. However, in the RG color space, the color of the image changes along the hemoglobin change axis AX1 in the inflamed portion where inflammation is most advanced, and changes along the mucosal change axis AX2 in the inflamed area where the degree of inflammation is the least. In addition, it is presumed that the color of the image of the inflamed portion where the degree of inflammation is intermediate changes with the same tendency. That is, the pixel correspondence point corresponding to the inflamed portion shifts in the azimuth angle direction starting from the reference point O' when the brightness of the pixel changes depending on the condition under the illumination light. In other words, when the brightness of the pixel changes depending on the condition under the illumination light, the pixel correspondence point corresponding to the inflamed portion moves while maintaining the deviation angle θ with respect to the hemoglobin change axis AX1 so that the distance from the reference point O' changes. This means that the deviation angle θ is a parameter that is substantially unaffected by changes in the brightness of the image.

The smaller the deviation angle θ, the stronger the R component with respect to the G component, indicating that the degree of redness in the lesion portion is relatively large. Further, the larger the deviation angle θ, the stronger the G component with respect to the R component, indicating that the degree of redness is relatively small. Therefore, the image evaluation value calculation unit 220b normalizes the angle θ so that the value becomes 255 when the deviation angle θ is zero and the value becomes zero when the deviation angle θ is $θ_{MAX}$. Further, $θ_{MAX}$ is equal to the angle formed by the hemoglobin change axis AX1 and the mucosal change axis AX2. That is, the evaluation value calculation unit 220b calculates the value in a range of 0 to 255, for each pixel of interest, which is obtained by normalizing the deviation angle θ calculated based on the information of the color component of the pixel of interest as the living tissue redness (pixel evaluation value).

The pixel of interest is selected one by one for all the pixels of the image. In the example illustrated in FIG. 4, the RG color space is used as the color space, but the RB color space can be used instead of the RG color space.

The image evaluation value calculation unit 220b calculates the living tissue redness, which is a value obtained by normalizing the deviation angle θ, as the pixel evaluation value. In some cases, the whiteness of the living tissue indicating the intensity of characteristic of the ulcer of the living tissue can also be calculated as a pixel evaluation value. For example, the pixel value of each color component of each pixel of the image of the living tissue is adjusted to give a linear gain (gain), and tone enhancement processing for increasing the effective resolution of the color expression is performed by substantially widening a dynamic range near the color gamut peculiar to the lesion. For example, an ulcer part containing white moss and purulent mucus of ulcerative colitis can be distinguished from an inflamed portion and a healthy portion by the color component. The ulcer portion is white, while the inflamed portion including edema and bleeding is red, and the healthy portion is yellow or green. The whiteness of the living tissue can be calculated using a deviation angle with respect to the reference axis which is different from the hemoglobin change axis AX1, which is expressed on the color space having two color components (two of R component, G component, and B component) as illustrated in FIG. 4 or three color components (R component, G component, and B component) as the coordinate axes. The tone enhancement processing is performed by the preprocessing unit 220a.

The image evaluation value calculation unit 220b calculates one image evaluation value using the pixel evaluation value of each pixel, for example, the above-mentioned living tissue redness. The image evaluation value calculation unit 220b may calculate, for example, the integrated value or the average value of the pixel evaluation values of all the pixels in the captured image as one image evaluation value, or may select pixels representing the image of the living tissue to be evaluated in the captured image and calculate the integrated value or the average value of the pixel evaluation values of the selected pixels as one image evaluation value. Alternatively, for example, among the RGB color component or pixel brightness component for each pixel, the pixels to be evaluated are extracted based on the color components or brightness components in a predetermined range, and the average value of the pixel evaluation values of the extracted pixels are obtained, or integration processing is performed, so that the image evaluation value calculation unit 220b may calculate one image evaluation value. The pixel portion to be evaluated in the image is a portion having a value of the color component within a predetermined range assumed in the living tissue in order to evaluate the degree of inflammation in an organ with high accuracy, and is preferably a portion of the pixel having a brightness component equal to or more than a predetermined value which is illuminated with an illumination light.

The image evaluation value calculated by the image evaluation value calculation unit 220b is sent to the organ lesion evaluation unit 220e.

The image evaluation value calculation unit 220b further creates a color map image in which the image of the living tissue is mosaicked with a display color that changes according to the living tissue redness. In order to create the color map image, a table in which the pixel evaluation value and the predetermined display color are associated with each other is stored in the storage area of the memory 204. In the above table, for example, different display colors are associated with each value in increments of 5. For example, blue is associated with a pixel evaluation value in a range of 0 to 5, and different display colors are associated according to the order of colors in the color wheel every time the pixel evaluation value increases by 5, and red is associated with the pixel evaluation value in a range of 250 to 255. The display color is a color that approaches a warm color from a cold color, for example, from blue to yellow to red as the living tissue redness increases. The image evaluation value calculation unit 220b determines the display color of the selected pixel of interest on the color map image based on the above table according to the living tissue redness of the pixel of interest.

In this way, the image evaluation value calculation unit 220b creates a color map image in which colors are added according to the pixel evaluation value (living tissue redness).

The imaging position information acquisition unit 220c acquires the imaging position information sent from a position measurement system 250 provided in the electronic endoscope system 1 in association with the captured image. The position measurement system 250 uses a sensor to acquire, for example, the position of the solid-state image sensor 108 located at the tip end portion of the electronic scope 100 inserted into the organ, and the position of each of the subsequent flexible tubes. The system, the system that acquires the insertion length of the electronic scope 100 inserted from the opening of the organ, or the captured image is displayed on the monitor 300, and the operator who sees this image manually gives an input instruction. An example is a system that acquires a specific part passing signal indicating that the tip of the electronic scope 100 has passed through a characteristic portion in the inserted organ.

In the system that acquires the position of the solid-state image sensor 108 using a sensor, for example, a plurality of magnetic sensors are provided at positions near the solid-state image sensor 108 at the tip end portion of the electronic scope 100 and in the flexible tube following the tip end portion to the electronic endoscopy processor 200 side at predetermined intervals. The magnetic fields having different intensities depending on positions are applied from the outside of the human body to which the electronic scope 100 is inserted to the organ to measure the intensities of the magnetic fields by the magnetic sensor. Thereby, the position of the magnetic sensor provided at the tip end portion can be known, and the curved shape in the organ of the flexible tube can be known from the positions of the plurality of magnetic sensors. As a result, the position of the tip end portion of the solid-state image sensor 108 can be known, and the shape of the electronic scope 100 in the organ and the insertion length of the organ of the electronic scope 100 from the open end can be known.

In the case of a system that acquires the insertion length of the electronic scope 100 inserted from the open end of an organ, for example, the moving distance information regarding how much the living tissue has moved between frame images having the adjacent imaging time in the captured moving image is acquired using the processing of the optical flow, and the moving distance information is integrated as the frame image changes to calculate the moving distance, so that the information of the current insertion length of the electronic scope 100 can be acquired. Further, for example, the information of the current insertion length of the electronic scope 100 can be acquired by measuring the length of the flexible tube extending from the tip end portion of the inserted electronic scope 100 toward the inside of the organ.

In a system that acquires a signal passing through a specific part of an organ, while the operator sees the image displayed on the monitor 300, the operator presses the button at hand to generates a specific part passing signal at a time point when an identifiable specific part inside the organ appears in the image and passes through, and the imaging position information acquisition unit 220c can acquire this specific part passing signal. The positions of specific parts inside the organ are, for example, when the organ is the large intestine, a position where an ascending colon begins, a position where the ascending colon ends and the large intestine bends and a transverse colon begins, and a position where the transverse colon ends, the large intestine bends, and a descending colon starts, a position where the descending colon ends, the large intestine bends, and the sigmoid colon begins, a position where the sigmoid colon ends and the rectum begins, and a position where the rectum ends and reaches the anus.

The information on the imaging position acquired by the imaging position information acquisition unit 220c is sent to the organ lesion evaluation unit 220e.

The lesion position calculation unit 220d determines the presence or absence of a lesion in each image based on whether the image evaluation value calculated by the image evaluation value calculation unit 220b exceeds a predetermined threshold, and a start position and an end position of the region of the lesion portion where the lesion is continuously spreading in the depth direction inside the organ. The threshold for determining the presence or absence of a lesion is set using a previously captured image previously evaluated by a doctor as having a lesion.

According to one embodiment, when lesions are present at a plurality of locations, it is preferable that the lesion position calculation unit 220d uses the lesion having the maximum length in the depth direction in which the lesions are continuously spread as a lesion portion to be evaluated. Of the plurality of lesion portions, the lesion portion with the largest length of the lesion portion is most dominant over the degree of lesion in the organ, and the degree (severity) of lesion in the organ is accurately evaluated. Therefore, it is preferable that the lesion portion having the maximum length in the depth direction inside the organ is a lesion portion to be evaluated.

The organ lesion evaluation unit 220e uses the length of the lesion portion to be evaluated calculated from the obtained start position and end position of the lesion portion as the extent information, and evaluates the degree of lesion in the organ using the extent information and the representative value of the image evaluation value of the captured lesion portion image of the lesion portion obtained by imaging the lesion portion to be evaluated. Here, the representative value is a statistic regarding the image evaluation values of a plurality of captured lesion portion images, and is, for example, a maximum value, a median value, or an average value. In particular, the representative value is preferably the maximum value because it is used as an index for handling the intensity of lesion in the lesion portion.

Figure 5:
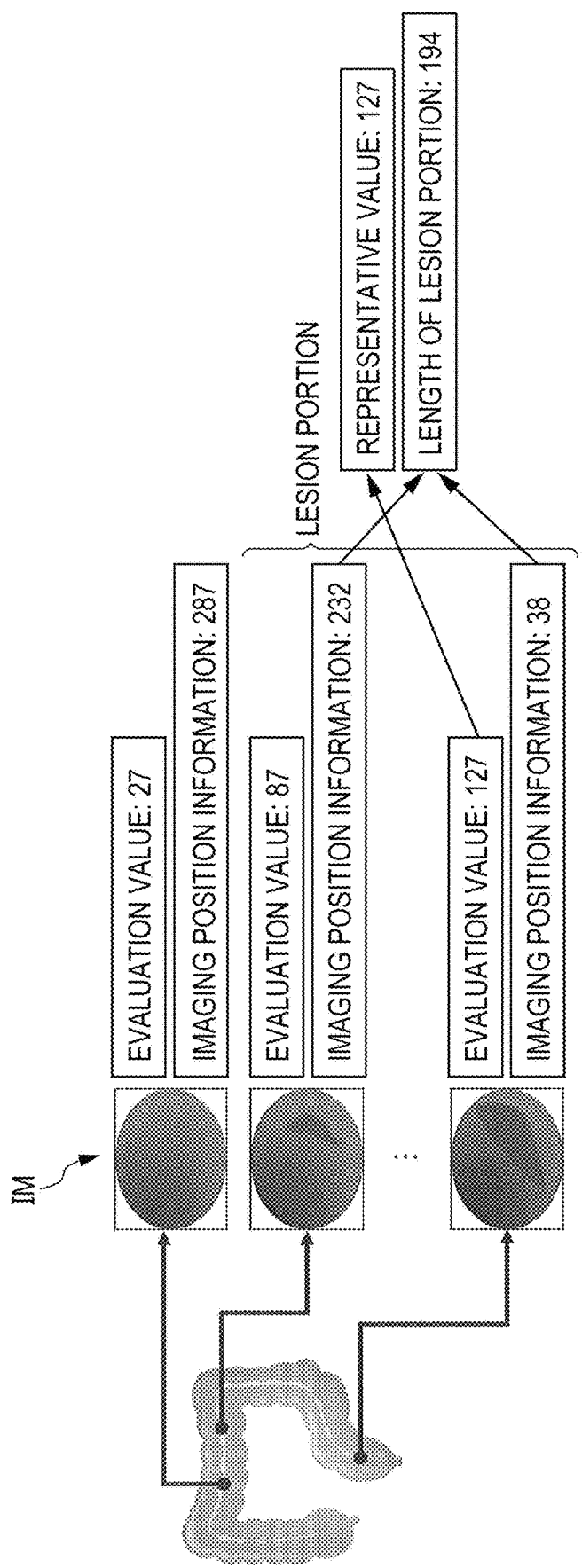
FIG. 5 is a diagram for explaining an example of processing performed by an organ lesion evaluation unit of one embodiment.

FIG. 5 is a diagram for explaining an example of processing performed by the organ lesion evaluation unit 220e. FIG. 5 exemplifies the image evaluation value (described as "evaluation value" in FIG. 5) and the imaging position information of each of the images IM inside the large intestine captured. In the example illustrated in FIG. 5, the position of the imaging position information "232" is the start position of the lesion portion, and the position of the imaging position information "38" is the end position of the lesion portion. That is, the range of the lesion portion is the range from the position of the imaging position information "232" to the position of the imaging position information "38". Therefore, the length of the lesion portion is "194" (=232-38).

Further, in the example illustrated in FIG. 5, the representative value is an example using the maximum value of the image evaluation value in the captured lesion portion image. In the example illustrated in FIG. 5, the image evaluation value in the captured lesion portion image at the position of the imaging position information "38" becomes the maximum value which is used as the representative value. Therefore, the representative value is "127".

According to one embodiment, the information on the extent of lesion is preferably area information indicating the extent of lesion portion. At each location from the start position to the end position of the lesion, the lesion does not exist over the entire inner circumference of the organ, and the lesion may be unevenly distributed in a part of the inner circumference of the organ. In some cases, it is more accurate to use the area information as the extent information of the lesion portion than to use the length of the lesion portion as the extent information of the lesion portion. In a case where the extent of the lesion portion is expressed by the area information, the area information of the lesion portion determined from the pixels determined as the part of the lesion in the captured lesion portion image is used in each of the captured lesion portion images obtained by imaging the lesion portion between the start position and the end position. It is possible to determine the pixel determined as the lesion portion in the captured lesion portion image as a lesion portion using the pixel evaluation value for each pixel used when calculating the image evaluation value and using the living tissue redness in the example where the inflammation evaluation value is calculated as an image evaluation value. Specifically, a pixel whose living tissue redness is equal to or higher than a preset threshold is defined as a lesion (inflammation) portion.

According to one embodiment, the organ lesion evaluation unit 220e counts the number of pixels in which the pixel evaluation value (for example, the living tissue redness) is equal to or greater than the threshold for determining a lesion in each of a plurality of captured lesion portion images. It is preferable to obtain the area information of the lesion portion based on the number of pixels counted in the entire captured lesion portion image. As the area information, the number of counted pixels multiplied by a predetermined coefficient may be used, or the number of pixels itself may be used. In this case, it is preferable to adjust the frame rate of imaging or the moving speed of the electronic scope so that the same lesion portion is not duplicated in the different captured lesion portion image.

According to one embodiment, it is preferable that the organ lesion evaluation unit 220e obtains an occupancy ratio of the pixel evaluation value (for example, the living tissue redness) in the captured lesion portion image to the image of the pixel equal to or higher than the threshold for determining a lesion for each captured lesion portion image, and obtains the area information based on an average value of the occupancy ratios in the entire captured lesion portion image and the length of the lesion portion calculated from the start position and the end position. As the area information, the product may be multiplied by a predetermined coefficient, or the product itself may be used. Since the average value of the occupancy ratios can be regarded as the ratio of the lesion portion to the inner circumference inside the organ, the product of the average value of the occupancy ratios and the length of the lesion portion can be used as an index of the area information of the lesion area.

In this way, the organ lesion evaluation unit 220e evaluates the degree of lesion in the organ by using the obtained extent information and the representative value of the image evaluation value. According to one embodiment, the evaluation of the degree of lesion in the organ is preferably performed as follows.

Specifically, the organ lesion evaluation unit 220e calls a lesion sample correspondence, from the memory 204, in which lesion sample extent information indicating a lesion sample representative value and the extent of a lesion portion of the lesion sample is associated with a known evaluation level corresponding to the image group of the lesion sample for each lesion sample obtained by using an image group of a plurality of lesion samples for which the evaluation level regarding the degree of lesion is determined, and holds the relationship. The lesion sample representative value and the extent information of the lesion portion of the lesion sample are preferably calculated by the same method as the above-described method of calculating the representative value and the extent information of the lesion portion to be evaluated. The image group of the lesion sample includes images of a plurality of lesion samples obtained by imaging the inside of the organ, and the degree of lesion in this lesion sample is evaluated by the level, and the evaluation level has already been determined. The image group of the lesion sample is preferably one evaluated by a doctor at an evaluation level such as Mayo score. The organ lesion evaluation unit 220e evaluates the degree of lesion to be evaluated at the evaluation level using the lesion sample correspondence from the extent information of the lesion portion which is obtained by imaging the inside of the organ and evaluated, and the representative value of the lesion portion to be evaluated.

Regarding the lesion sample correspondence, for example, by preparing a plurality of sets of lesion samples and performing regression analysis on the representative value in the image group of the lesion sample and the evaluation level of the lesion sample with respect to the lesion sample extent information to obtain a regression equation, so that a lesion sample correspondence can be established. In addition, by performing cluster analysis of multiple sets of image groups of the lesion samples, a plurality of clusters are created based on the lesion sample representative value and lesion sample extent information of the lesion sample image group, and evaluation levels are given to each cluster, so that a lesion sample correspondence can be created. In addition, a plurality of sets of image groups of the lesion samples having a fixed evaluation level are prepared, and the lesion sample representative value, the lesion sample extent information, and the evaluation level of the corresponding lesion sample are used as learning data. The lesion sample correspondence between the representative value and the lesion sample extent information in the image group of the lesion sample and the evaluation level of the lesion sample may be machine-learned by a predictive model, and the machine-learned predictive model may be provided in the organ lesion evaluation unit 220e. This predictive model can predict the evaluation level of the lesion part to be evaluated from the extent information of the lesion part to be evaluated and the representative value of the lesion portion to be evaluated. That is, the lesion sample correspondence also includes the correspondence based on artificial intelligence constructed by machine learning. For machine learning of the predictive model, for example, deep learning by a neural network is used. In addition, a random forest using a tree structure can be used. As the predictive model, a known model such as a convolutional neural network can be used.

Figure 6:
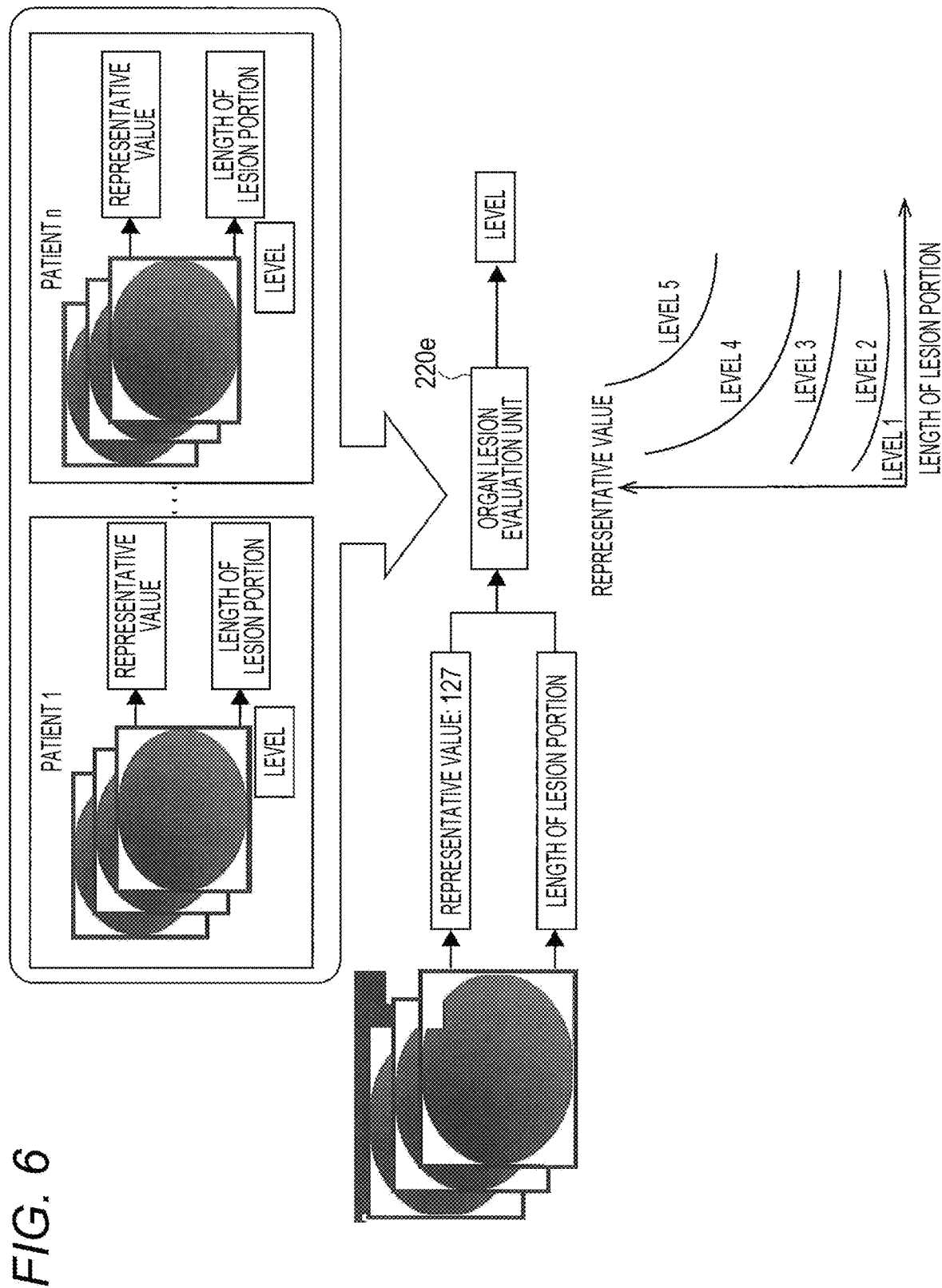
FIG. 6 is a diagram for explaining an example in which the organ lesion evaluation unit of one embodiment calculates a level from extent information of the lesion portion to be evaluated and a representative value of the lesion portion to be evaluated.

FIG. 6 is a diagram for explaining an example in which the organ lesion evaluation unit 220e calculates the evaluation level from the extent information of the lesion portion to be evaluated and the representative value of the lesion sample to be evaluated by using the lesion sample correspondence. The image group of the plurality of sets of lesion samples includes the image group of the lesion samples of Patient 1, . . . , Patient n and the evaluated levels of the associated lesion samples. In FIG. 6, the evaluation level is described as "level". From this image group, the lesion sample representative value and the length of the lesion portion (lesion sample extent information) in the lesion sample are calculated and set. A plurality of sets of image groups of such lesion samples are prepared, and a lesion sample correspondence for associating between the lesion sample representative value and the lesion sample extent information and the evaluation level is constructed and stored in the memory 204. When evaluating the degree of lesion to be evaluated, the organ lesion evaluation unit 220e calls and holds the lesion sample correspondence, and uses this correspondence to predict and determine the evaluation level from the length (extent information) of the lesion sample to be evaluated and the representative value of the lesion portion to be evaluated.

In this way, the organ lesion evaluation unit 220e evaluates the degree of lesion in the organ using the extent information of the lesion portion to be evaluated calculated from the start position and the end position of the lesion portion to be evaluated and the representative value of the image evaluation value of the captured lesion portion image, so that the degree of lesion can be comprehensively evaluated.

The evaluation result integration unit 220f creates a screen for displaying, in the monitor 300, an evaluation level evaluated by the organ lesion evaluation unit 220e, a two-dimensional scatter diagram as necessary, a captured lesion portion image in which the image evaluation value becomes a maximum value, and a color map image processed from this image. In the two-dimensional scatter diagram, one of the horizontal axis and the vertical axis is the axis of the representative value of the lesion portion, and the other of the horizontal axis and the vertical axis is the axis of the extent information of the lesion portion. The representative value of the lesion portion to be evaluated and the extent information of the lesion portion to be evaluated are plotted together with the lesion sample representative value and the lesion sample extent information.

On such a screen, or separately from this screen, an image of the inside of the organ may be reproduced as a moving image.

Since the monitor 300 displays the two-dimensional scatter diagram in which the representative value of the lesion portion to be evaluated and the extent information of the lesion portion to be evaluated are plotted in a screen, the operator can easily grasp the severity of the lesion portion to be evaluated.

Figure 7A:
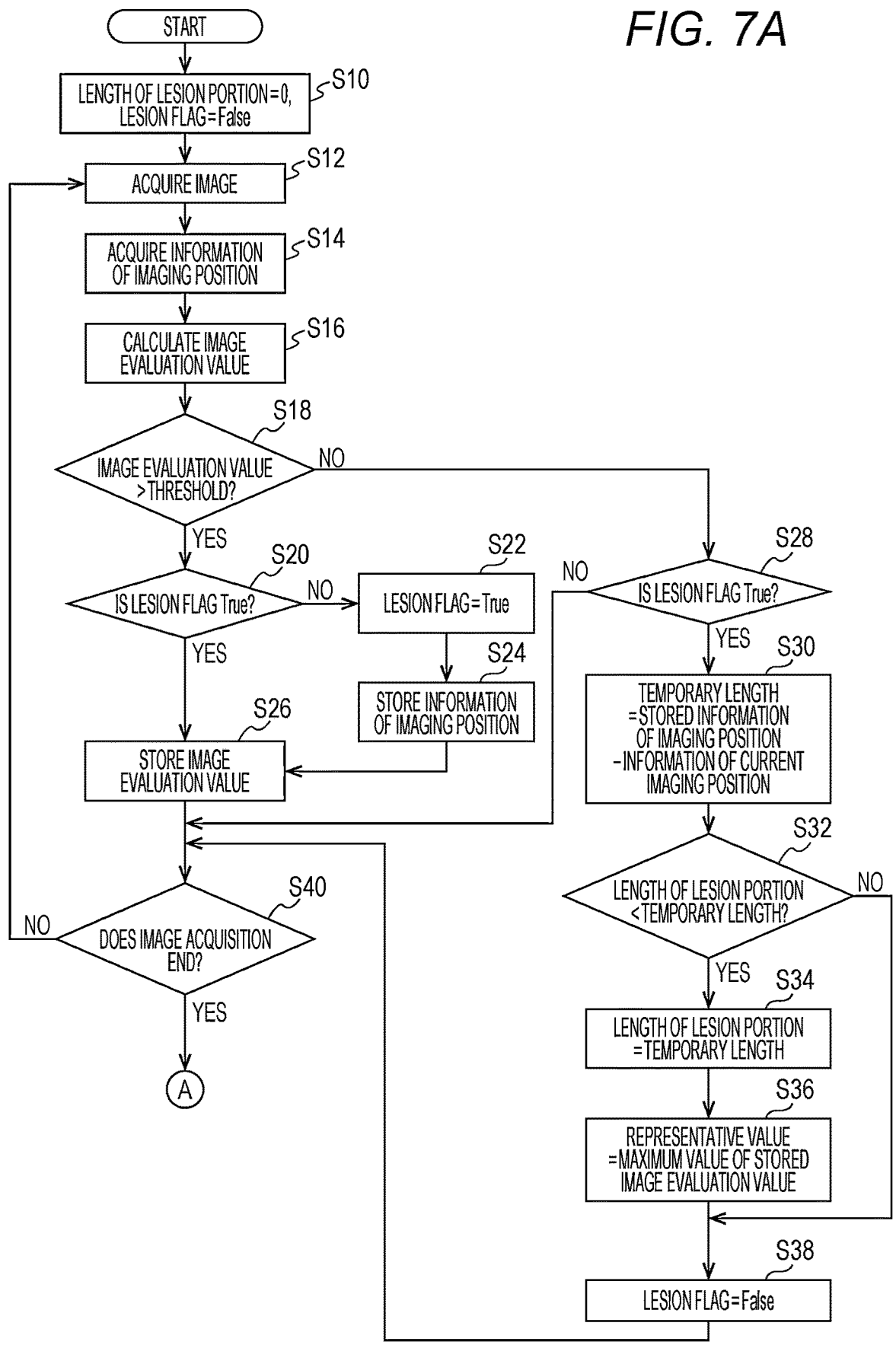
FIG. 7A is a diagram illustrating an example of a processing flow for calculating the degree of lesion in an organ from the acquisition of an image performed by the image processing unit of one embodiment.
Figure 7B:
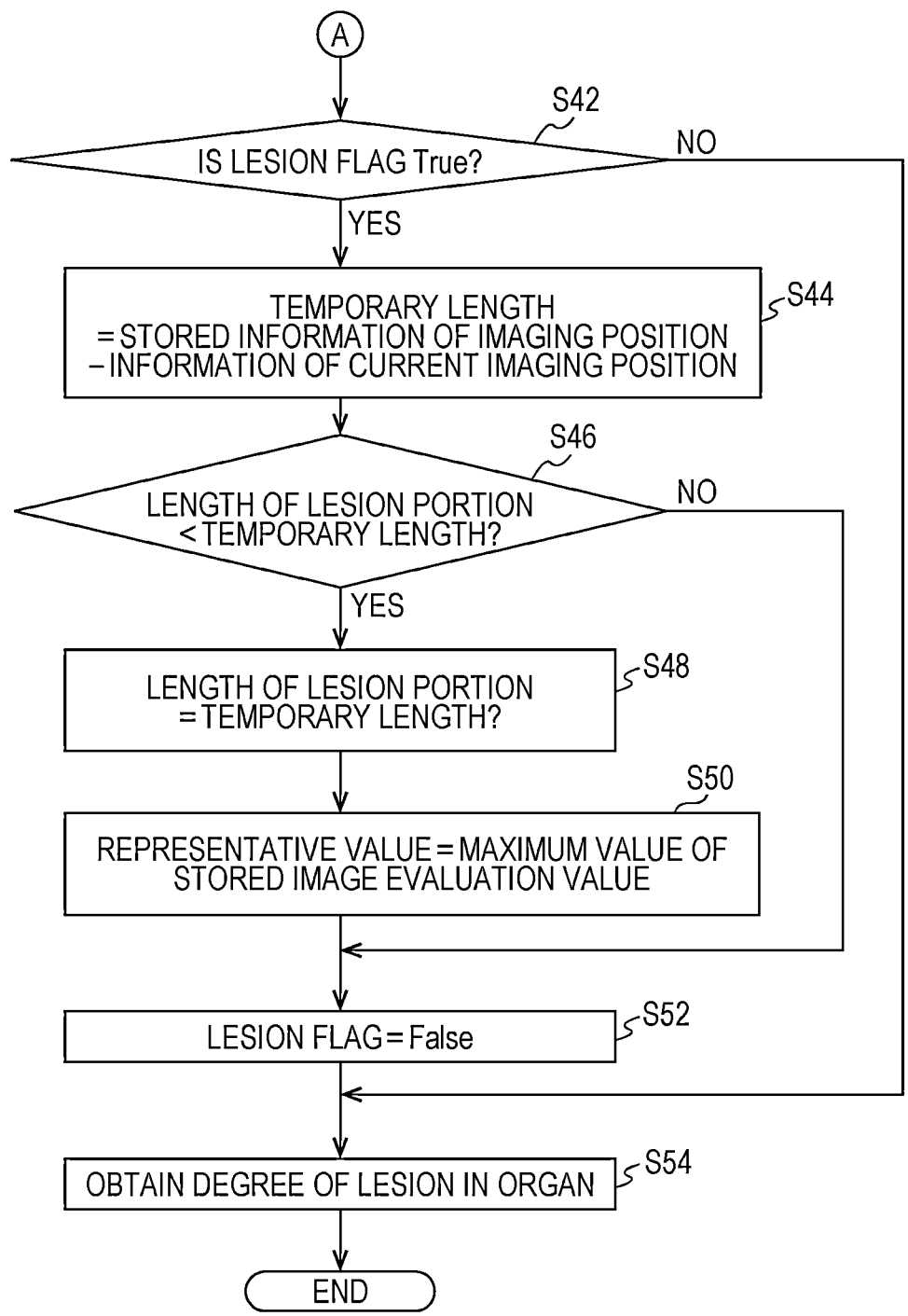
FIG. 7B is a diagram illustrating an example of a processing flow for calculating the degree of lesion in an organ from the acquisition of an image performed by the image processing unit of one embodiment.

FIGS. 7A and 7B are diagrams illustrating an example of a flow of processing for calculating the degree of lesion in an organ from the acquisition of images performed by the evaluation unit 225. The illustrated flow is an example in which the representative value is the maximum value of the image evaluation values, and the lesion portion to be evaluated is an example in which the maximum length of a plurality of lesion portions in the organ is evaluated symmetrically.

First, in the evaluation unit 225, the length of the lesion portion and a lesion flag, which are internal variables, are set. Specifically, the length of the lesion portion is set to zero, and the lesion flag indicating the presence or absence of the lesion portion is set to "False" (False indicates that the lesion does not exist) (Step S10). The lesion flag is either "False" or "True".

Next, the preprocessing unit 220a acquires an image (Step S12), and performs the above-mentioned RGB conversion, color space conversion, reference axis setting, and color correction processing.

Further, the imaging position information acquisition unit 220c acquires the imaging position information associated with the image acquired by the preprocessing unit 220a from the position measurement system 250 (Step S14). On the other hand, the image evaluation value calculation unit 220b calculates the image evaluation value using the image processed by the preprocessing unit 220a (Step S16). The organ lesion evaluation unit 220e determines whether the calculated image evaluation value exceeds a threshold for determining the presence or absence of a lesion (Step S18). If this determination result is affirmative, the organ lesion evaluation unit 220e determines whether the lesion flag is "True" (Step S20). If this determination result is negative, that is, if the lesion flag is "False", the lesion position calculation unit 220d sets the lesion flag to "True" because the lesion portion has been detected (Step S22). Further, the information of the current imaging position acquired in Step S14 is stored in the memory 204. As a result, the information of the start position of the lesion portion is stored in the memory 204. Further, the process proceeds to Step S26 described later.

On the other hand, if the determination result in Step S20 is affirmative, that is, if the lesion flag is "True", it indicates that the lesion portion is continuously occurring, so that the organ lesion evaluation unit 220e stores the image evaluation value calculated in Step S16 in the memory 204 (Step S26). That is, the image evaluation value in the lesion portion is sequentially stored in the memory 204. After that, the preprocessing unit 220a determines whether the acquisition of the image is completed (Step S40). When the acquisition of the image is continued (when the determination result is negative), the process proceeds to Step S12, and the preprocessing unit 220a acquires a new image and continues the process. When the acquisition of the image is completed, the process proceeds to the determination of whether the lesion flag illustrated in FIG. 7B is "True" (Step S42).

On the other hand, if the determination result in Step S18 is negative, the organ lesion evaluation unit 220e determines whether the lesion flag is "True" (Step S28). If this determination result is affirmative, the end position is determined assuming that the current imaging position is at the end position of the lesion portion. Therefore, the lesion position calculation unit 220d determines as a temporary length a value obtained by subtracting the information of the current imaging position from the information of the imaging position stored in the memory 204, that is, the information of the position of the start point of the lesion portion (Step S30). Further, the organ lesion evaluation unit 220e determines whether the determined temporary length is larger than the length of the lesion portion, which is an internal variable (Step S32). If this determination result is affirmative, the lesion position calculation unit 220d sets the determined temporary length as the length of the lesion portion (Step S34). Further, the organ lesion evaluation unit 220e sets the maximum value among the image evaluation values stored in the memory 204 as a representative value (Step S36). After this, the organ lesion evaluation unit 220e sets the lesion flag to "False" (Step S38), and proceeds to Step S40.

On the other hand, if the determination result in Step S28 is negative, the process proceeds to Step S40 described above. That is, if the determination result in Step S28 is negative, the lesion portion is still not found, and the process proceeds to the evaluation of the image to be acquired next.

Further, when the determination result in Step S32 is negative, that is, when the temporary length is shorter than the length of the lesion portion already set, this lesion portion has a small effect on the degree of lesion of the organ, and thus is not regarded as an evaluation target. At this time, since the lesion portion is completed at the current imaging position, the process proceeds to Step S38 in which the lesion flag is set to "False". After this, the process proceeds to Step S40.

Although the acquisition of the image is completed, the processes of Steps S42 to S50 are performed in consideration of the case where the lesion portion continues in the last acquired image. That is, the organ lesion evaluation unit 220e determines whether the lesion flag is "True". If the determination result is affirmative, that is, if the lesion flag is "True", it means that the lesion portion continues even in the last acquired image, so the same processes as in Steps S30 to S38 are performed (Steps S44 to S52). Since the processes of Steps S44 to 52 are the same as those of Steps S30 to 38, the description thereof will be omitted.

In this way, the organ lesion evaluation unit 220e obtains the degree of lesion in the organ at the evaluation level from the length of the lesion portion having the maximum length in the organ and its representative value using the above-mentioned preset correspondence (Step S54).

In this way, the electronic endoscope system 1 can obtain information on the intensity of lesion in the lesion portion and the extent of lesion by processing the acquired image, so that it is possible to comprehensively evaluate the degree of lesion in the organ.

The above has described the endoscope system of the present invention in detail. The endoscope system of the present invention are not limited to the above-described embodiment, and may of course be modified or altered in various ways in a range not deviating from the scope and spirit of the present invention.

REFERENCE SIGNS LIST 1 electronic endoscope system
100 electronic scope
200 processor
220 image processing unit
225 evaluation unit
220a preprocessing unit
220b image evaluation value calculation unit
220c imaging position information acquisition unit
220d lesion position calculation unit
220e organ lesion evaluation unit
220f evaluation result integration unit
225 evaluation unit
230 light source unit
250 position measurement system
300 monitor
400 printer
600 server

The invention claimed is:

1. An electronic endoscope system for evaluating a lesion of a living tissue in an organ of a living body, comprising:
an electronic endoscope configured to image the living tissue in the organ configured to be inserted into the organ at different depths and having
  a light carrying bundle extending through at least a portion of the electronic endoscope in a longitudinal direction thereof and configured to carry light from a light source beyond a first end of the light carrying bundle to a second end of the light carrying bundle,
  a light distribution lens positioned at a first end of the electronic endoscope and in front of the first end of the light carrying bundle and configured to distribute light from the first end of the light carrying bundle to illuminate the living tissue in the organ when the electronic endoscope is inserted into the living body,
  an objective lens also positioned at the first end of the electronic endoscope and spaced from the light distribution lens and configured to receive light from the living tissue illuminated by the light from the distribution lens, and
  a charge coupled device positioned behind the objective lens to receive light from the living tissue of the organ at different depths of the organ through the objective lens and configured to generate a plurality of captured images at different depths of the organ;
a processor configured to process the plurality of captured images of the living tissue at different depths of the organ received from the charge coupled device to evaluate a severity of the lesion in the organ; and
a monitor configured to display an evaluation result of the lesion on a screen,
wherein the processor is configured to evaluate the severity of the lesion in the organ by
  calculating an image evaluation value, reflecting a progression of the lesion in the living tissue, for each of the plurality of captured images of the living tissue, the severity of the lesion being determined from the image evaluation values and a length of the lesion,
  acquiring position information at imaging positions at the different depths in the organ in which each of light images are captured by the objective lens, in association with each of the captured images generated by the charge coupled device,
  determining the presence or absence of the lesion in each of the captured images generated by the charge coupled device in a depth direction inside the organ, the processor determining the presence of the lesion in captured images generated by the charge coupled device when the image evaluation value of the captured images generated by the charge coupled device exceeds a predetermined threshold,
  obtaining a start position and an end position of the lesion, which is continuously spreading in the depth direction inside the organ, to determine a length of the lesion in the depth direction by determining the presence or absence of the lesion in each of the captured images generated by the charge coupled device in the depth direction inside the organ,
  setting the length of the lesion from the obtained start position and the end position of the legion, and
  evaluating the severity of lesion in the organ using the set length of the legion and a representative value of the image evaluation values of the plurality of captured images generated by the charge coupled device of the lesion.

2. The electronic endoscope system according to claim 1, wherein the processor is configured to use, when the lesions exist at a plurality of locations, one having a maximum length in the depth direction in which the lesion is continuously spread as the lesion to be evaluated.

3. The electronic endoscope system according to claim 1, wherein the representative value is a maximum value among the image evaluation values of a captured lesion image generated by the charge coupled device.

4. The electronic endoscope system according to claim 1, wherein
a memory is configured to store a sample-lesion correspondence between
  a known evaluation level of the degree of severity of a previously-obtained sample lesion for each of previously-obtained lesion samples whose previously-obtained captured images generated by the charge coupled device are obtained from a plurality of previously-obtained captured images generated by the charge coupled device of an inside of the organ, and
  a combination of the lesion-sample length of the previously-obtained sample lesion and a lesion-sample representative value of image evaluation values of the previously-obtained sample lesion,
the processor is configured to
  obtain from the memory the sample-lesion correspondence and
  evaluate the degree of severity of a lesion to be evaluated at the evaluation level using the lesion-sample correspondence, the length of the lesion to be evaluated obtained by imaging an inside of the organ, and the representative value of the lesion to be evaluated.

5. The electronic endoscope system according to claim 4, wherein
the processor is configured to
  generate a predictive model for predicting the evaluation level of the lesion to be evaluated,
  set a lesion-sample representative value of a previously-obtained lesion sample corresponding to the representative value, the lesion-sample length corresponding to the length the lesion, and the evaluation level as learning data for each of the previously-obtained lesion samples obtained using the image group including images of the plurality of previously-obtained lesion samples having the determined evaluation level of the severity of the lesion, obtain the predictive model by machine-learning of a correspondence between the lesion-sample representative value, the lesion-sample length and the evaluation level, and cause the predictive model to predict an evaluation level of the lesion to be evaluated from the representative value of the lesion to be evaluated and the length of the lesion portion.

6. The electronic endoscope system according to claim 4, wherein the monitor is configured to display a two-dimensional scatter diagram on the screen, in which the representative value of the lesion to be evaluated and the length of the lesion to be evaluated are plotted together with the lesion-sample representative value and the lesion-sample length.

7. An electronic endoscope system for evaluating a lesion of a living tissue in an organ of a living body, comprising:

an electronic endoscope configured to image the living tissue in the organ configured to be inserted into the organ at different depths and having a light carrying bundle extending through at least a portion of the electronic endoscope in a longitudinal direction thereof and configured to carry light from a light source beyond a first end of the light carrying bundle to a second end of the light carrying bundle, a light distribution lens positioned at a first end of the electronic endoscope and in front of the first end of the light carrying bundle, and configured to distribute light from the first end of the light carrying bundle to illuminate the living tissue in the organ when the electronic endoscope is inserted into the living body, an objective lens also positioned at the first end of the electronic endoscope and spaced from the light distribution lens and configured to receive light from the living tissue illuminated by the light from the distribution lens, and a charge coupled device positioned behind the objective lens to receive light from the living tissue of the organ at different depths of the organ through the objective lens and configured to generate a plurality of captured images at different depths of the organ;

a processor configured to evaluate a severity of the lesion of the living tissue in the organ by processing the plurality of captured images of the living tissue at different depths of the organ and received from the charge coupled device; and a monitor configured to display an evaluation result of the lesion in a screen, wherein the processor is configured to perform the evaluation by calculating a pixel evaluation value, reflecting a progression of the lesion of the living tissue, for each pixel of the plurality of captured images of the living tissue, calculating an image evaluation value, reflecting the progression of the lesion of the living tissue, for each of the plurality of captured images of the living tissue from the pixel evaluation values for one of the captured images, the severity of the lesion being determined based on the image evaluation values, and an area over which the lesion extends, acquiring position information at imaging positions in the organ in which each of light images is captured by the objective lens, in association with each of the captured images generated by the charge coupled device, determining the presence or absence of the lesion in each of the captured images generated by the charge coupled device in a depth direction inside the organ, the processor determining the presence of the lesion in a captured images generated by the charge coupled device when the image evaluation value of the captured images generated by the charge coupled device exceeds a predetermined threshold, obtaining a start position and an end position of the lesion, which is continuously spreading in the depth direction inside the organ, to determine a length of the lesion in the depth direction by determining the presence or absence of the lesion in each of the captured images generated by the charge coupled device in the depth direction inside the organ, setting the area over which the legion extends by determining pixels having a pixel evaluation value equal to or greater than a threshold for determining the lesion in the plurality of captured images generated by the charge coupled device obtained by imaging the lesion between the start position and the end position, and evaluating the severity of lesion in the organ using the set area and a representative value of the image evaluation values of the plurality of captured images of the lesion generated by the charge coupled device.

8. The electronic endoscope system according to claim 7, wherein the processor is configured to obtain the area based on a number of pixels obtained by counting pixels whose pixel evaluation value is equal to or greater than the threshold for determining the lesion in the captured image generated by the charge coupled device.

9. The electronic endoscope system according to claim 7, wherein processor is configured to obtain the area based on a product of an average value in a captured image of the lesion of an occupancy ratio, in the captured image generated by the charge coupled device, of pixels whose pixel evaluation value is equal to or greater than the threshold for determining the lesion, and a length of the lesion to be evaluated calculated from the start position and the end position.

* * * * *